(12) United States Patent
Shou et al.

(10) Patent No.: US 12,073,332 B2
(45) Date of Patent: Aug. 27, 2024

(54) REST STOP RECOMMENDATION SYSTEM

(71) Applicant: Toyota Motor Engineering & Manufacturing North America, Inc., Plano, TX (US)

(72) Inventors: Zhenyu Shou, Milpitas, CA (US); Ziran Wang, San Jose, CA (US); Kyungtae Han, Palo Alto, CA (US); Yongkang Liu, Plano, TX (US); Prashant Tiwari, Santa Clara, CA (US)

(73) Assignee: Toyota Motor Engineering & Manufacturing North America, Inc., Plano, TX (US)

( * ) Notice: Subject to any disclaimer, the term of this patent is extended or adjusted under 35 U.S.C. 154(b) by 349 days.

(21) Appl. No.: 16/998,529

(22) Filed: Aug. 20, 2020

(65) Prior Publication Data

US 2022/0058495 A1    Feb. 24, 2022

(51) Int. Cl.

| | | |
|---|---|---|
| G06Q 30/02 | (2023.01) | |
| G01C 21/34 | (2006.01) | |
| G01C 21/36 | (2006.01) | |
| G06N 5/04 | (2023.01) | |
| G06N 7/01 | (2023.01) | |
| G06N 20/00 | (2019.01) | |
| G06Q 30/0201 | (2023.01) | |
| G06Q 50/14 | (2012.01) | |
| G16H 50/70 | (2018.01) | |

(52) U.S. Cl.
CPC .......... *G06N 5/04* (2013.01); *G01C 21/3492* (2013.01); *G01C 21/3682* (2013.01); *G06N 7/01* (2023.01); *G06N 20/00* (2019.01); *G06Q 30/0201* (2013.01); *G16H 50/70* (2018.01); *G06Q 50/14* (2013.01)

(58) Field of Classification Search
CPC .......... G10L 21/0208; G01C 21/3469; B60W 30/143; G05D 1/0221; G09B 9/042
See application file for complete search history.

(56) References Cited

U.S. PATENT DOCUMENTS

| | | |
|---|---|---|
| 8,022,831 B1 | 9/2011 | Wood-Eyre |
| 10,621,860 B2 | 4/2020 | Coelho de Azevedo |
| 2007/0161342 A1* | 7/2007 | Shirakashi ............. B24D 11/02 451/526 |

(Continued)

*Primary Examiner* — Saba Dagnew
(74) *Attorney, Agent, or Firm* — Christopher G. Darrow; DARROW MUSTAFA PC

(57) ABSTRACT

A rest stop recommendation system monitors driving behavior of a driver and stores information indicating the driving behavior as historical data, determines, based at least in part on the historical data, a driver tiredness state, a continuous driving length preference, and a refueling pattern preference, determines a time to recommend a rest stop based at least in part on the driver tiredness state, the continuous driving length preference, and the refueling pattern preference, extracts, from a map database, a plurality of rest stops within a predetermined radius of a position of the vehicle, determines rest stop characteristic preferences based at least in part on the historical data, selects one or more potential rest stops from among the plurality of rest stops based at least in part on the rest stop characteristic preferences, and presents the one or more potential rest stops to the driver in a recommendation.

18 Claims, 6 Drawing Sheets

(56) References Cited

U.S. PATENT DOCUMENTS

| | | |
|---|---|---|
| 2012/0072109 A1 | 3/2012 | Waite et al. |
| 2013/0282268 A1 | 10/2013 | Goerick et al. |
| 2015/0233727 A1 | 8/2015 | Roelle et al. |
| 2015/0253144 A1* | 9/2015 | Rau .................. G01C 21/343 |
| | | 705/348 |
| 2016/0046294 A1 | 2/2016 | Lee et al. |
| 2016/0086397 A1 | 3/2016 | Phillips |
| 2016/0109251 A1 | 4/2016 | Thakur |
| 2017/0103121 A1* | 4/2017 | Mori .................... G09B 9/042 |
| 2017/0174221 A1* | 6/2017 | Vaughn ............... G05D 1/0221 |
| 2017/0200449 A1* | 7/2017 | Penilla ................ G10L 15/063 |
| 2017/0261330 A1* | 9/2017 | Zhou .................. G01C 21/3469 |
| 2017/0370732 A1 | 12/2017 | Bender et al. |
| 2018/0209802 A1 | 7/2018 | Jung et al. |
| 2018/0345965 A1* | 12/2018 | Payne ............ B60W 30/18009 |
| 2018/0357894 A1 | 12/2018 | Bjersing et al. |
| 2020/0219316 A1 | 7/2020 | Baik et al. |
| 2021/0078539 A1* | 3/2021 | Gonzalez ............. B60R 25/305 |

\* cited by examiner

REST STOP RECOMMENDATION SYSTEM

TECHNICAL FIELD

The subject matter described herein relates, generally, to systems and methods for recommending a rest stop for a driver, and more particularly, to systems and methods that use historical data and digital twin technology to determine personalized rest stop recommendations and determine when to provide the recommendations without requiring the use of invasive internal sensors.

BACKGROUND

During a long trip it may be beneficial to a driver of a vehicle to have the vehicle periodically provide recommendations for a rest stop. Rest stop recommendations can be particularly useful in various situations, such as when a trip is on a remote highway and rest stops are spaced relatively far apart or when the driver has particular preferences for rest stops which may not always be met by typical rest stops. In conventional recommendation systems the vehicle is equipped with a wide array of sensors, such as cameras, temperature sensors, weight sensors, heat sensors, eye gaze sensors, and so on, to constantly monitor the driver and build a profile from which the conventional system may determine physiological signs that the driver is tired and thus ready to receive a rest stop recommendation. However, many drivers may feel uncomfortable being constantly watched, monitored and tracked by cameras, etc., and having so much data regarding their physiology stored in what may be an insecure system.

SUMMARY

The disclosed apparatuses, methods and systems relate to a rest stop recommendation system that uses historical data and digital twin technology to determine a personalized rest stop recommendation for a driver, as well as determine when to present the recommendation. Unlike conventional systems, the disclosed embodiments do not require the deployment of a multitude of internal sensors to constantly survey and analyze the driver or store personal physiological information captured from monitoring the driver.

In one embodiment, the disclosed vehicle rest stop recommendation system includes a map database and one or more processors. The system further includes a memory communicably coupled to the one or more processors and storing: a monitoring module including instructions that when executed by the one or more processors cause the one or more processors to monitor, over a period of time, driving behavior of an ego driver and store information indicating the driving behavior as historical data, a timing module including instructions that when executed by the one or more processors cause the one or more processors to determine, based at least in part on the historical data, a driver tiredness state, a continuous driving length preference, and a refueling pattern preference, and determine a time to recommend a rest stop based at least in part on the driver tiredness state, the continuous driving length preference, and the refueling pattern preference, and a location module including instructions that when executed by the one or more processors cause the one or more processors to, at the time to recommend a rest stop, extract from the map database a plurality of rest stops within a predetermined radius of a position of the vehicle, determine rest stop characteristic preferences based at least in part on the historical data, select one or more potential rest stops from among the plurality of rest stops based at least in part on the rest stop characteristic preferences, and present the one or more potential rest stops to the ego driver in a recommendation.

In one embodiment, a method of providing a personalized rest stop recommendation includes monitoring, over a period of time, driving behavior of an ego driver driving a vehicle and store information indicating the driving behavior as historical data, determining, based at least in part on the historical data, a driver tiredness state, a continuous driving length preference, and a refueling pattern preference, determining a time to recommend a rest stop based at least in part on the driver tiredness state, the continuous driving length preference, and the refueling pattern preference, extracting, from a map database, a plurality of rest stops within a predetermined radius of a position of the vehicle, determining rest stop characteristic preferences based at least in part on the historical data, selecting one or more potential rest stops from among the plurality of rest stops based at least in part on the rest stop characteristic preferences, and presenting the one or more potential rest stops to the ego driver in a recommendation.

In one embodiment, a non-transitory computer-readable medium for providing a personalized rest stop recommendation includes instructions that, when executed by one or more processors, cause the one or more processors to monitor, over a period of time, driving behavior of an ego driver driving a vehicle and store information indicating the driving behavior as historical data, determine, based at least in part on the historical data, a driver tiredness state, a continuous driving length preference, and a refueling pattern preference, determine a time to recommend a rest stop based at least in part on the driver tiredness state, the continuous driving length preference, and the refueling pattern preference, extract, from a map database, a plurality of rest stops within a predetermined radius of a position of the vehicle, determine rest stop characteristic preferences based at least in part on the historical data, select one or more potential rest stops from among the plurality of rest stops based at least in part on the rest stop characteristic preferences, and present the one or more potential rest stops to the ego driver in a recommendation.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, groups of boxes, or other shapes) in the figures represent one embodiment of the boundaries. In some embodiments, one element may be designed as multiple elements or multiple elements may be designed as one element. In some embodiments, an element shown as an internal component of another element may be implemented as an external component and vice versa. Furthermore, elements may not be drawn to scale.

DETAILED DESCRIPTION

Systems, methods, and other embodiments associated with a vehicle rest stop recommendation system are disclosed. The disclosed embodiments include a rest stop recommendation system that uses a data-driven approach to provide a driver with options of suitable rest areas that satisfy the driver's personal needs at a proper time. The disclosed rest stop recommendation system can first identify the driver's tiredness state during driving and then recommend a rest area that meets the driver's personalized preferences. Leveraging a digital twin framework, in which numerous historical trajectories of multiple drivers can be collected, the data-driven approach can determine the driver's tiredness state based on driving behavior patterns without resorting to any in-cabin sensing units that conventional systems deploy, which may raise privacy concerns.

A digital twin, as used herein, refers to a dynamic virtual representation of a driver-vehicle system across multiple trips, using real-time data to enable understanding, learning and prediction. The disclosed embodiments can implement a digital twin framework in which a digital twin of the driver-vehicle system is maintained in a cloud server or in local storage in the vehicle. The digital twin data can include multiple types of driving behavior and characteristics exhibited by the driver-vehicle system over time, such as speed, lane changing, length of time driven prior to a rest stop, amount of fuel remaining before stopping to refuel, and other aspects of driving as will be discussed further below.

Figure 1:
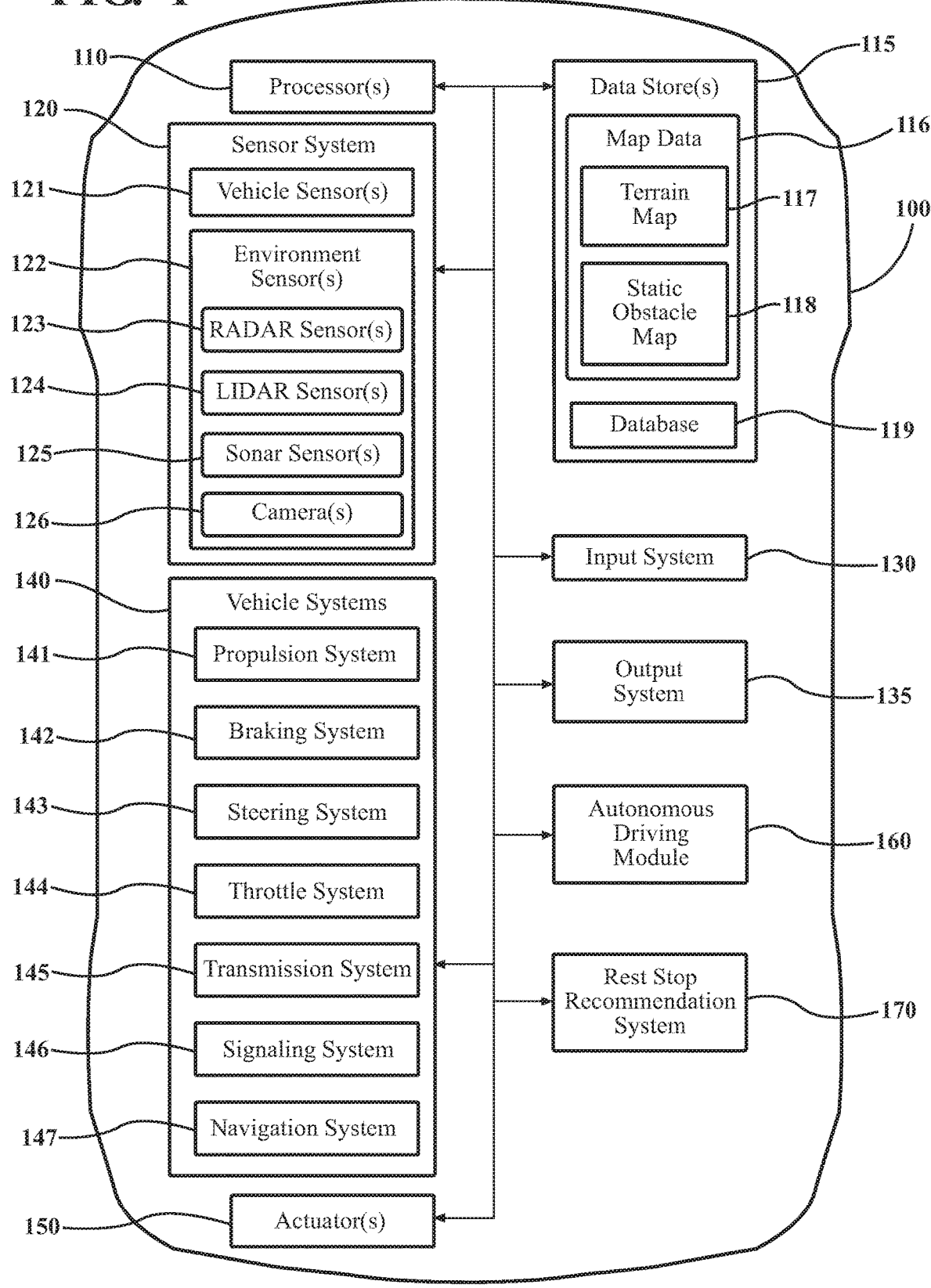
FIG. 1 illustrates one embodiment of a vehicle within which embodiments disclosed herein may be implemented.

Referring to FIG. 1, an example of a vehicle 100 that can implement one or more of the disclosed embodiments is illustrated. As used herein, a "vehicle" is any form of transport that is used for moving people, animals, goods, or the like. In one or more implementations, the vehicle 100 is an automobile. While arrangements will be described herein generally with respect to automobiles, it should be understood that the scope of the disclosed subject matter is not limited to automobiles. In some implementations, the vehicle 100 may be any form of powered, multi-wheeled transport or vehicle that a driver may driver for a trip during which rest stops would be useful and thus can benefit from the functionality discussed herein.

As shown in FIG. 1, the vehicle 100 includes multiple elements. It should be understood that in various embodiments the vehicle 100 may not necessarily include all of the elements shown in FIG. 1. The vehicle 100 can have any combination of the various elements shown in FIG. 1. Further, the vehicle 100 can have other elements in addition to those shown in FIG. 1. In some arrangements, the vehicle 100 may be implemented without one or more of the elements shown in FIG. 1. While the various elements are shown as being located within the vehicle 100 in FIG. 1, it should be understood that one or more of these elements can be located external to the vehicle 100. Further, the elements shown may be physically separated by large distances.

Some of the possible elements of the vehicle 100 are shown in FIG. 1 and will be described along with subsequent figures. However, a more detailed description of many of the elements in FIG. 1 will be provided after the discussion of FIGS. 2-7 for purposes of brevity in this description. For simplicity and clarity of illustration, where appropriate, reference numerals have been repeated among the different figures to indicate corresponding or analogous elements. In addition, while the discussion outlines numerous specific details to provide a thorough understanding of the embodiments described herein, those of ordinary skill in the art will understand that the embodiments described herein may be practiced using various combinations of these elements.

In any case, the vehicle 100 includes a rest stop recommendation system 170 that is implemented to perform methods and other functions as disclosed herein relating to determining when to provide a rest stop recommendation and personalizing the recommendation. The noted functions and methods will become more apparent in the following discussion of the figures.

Figure 2:
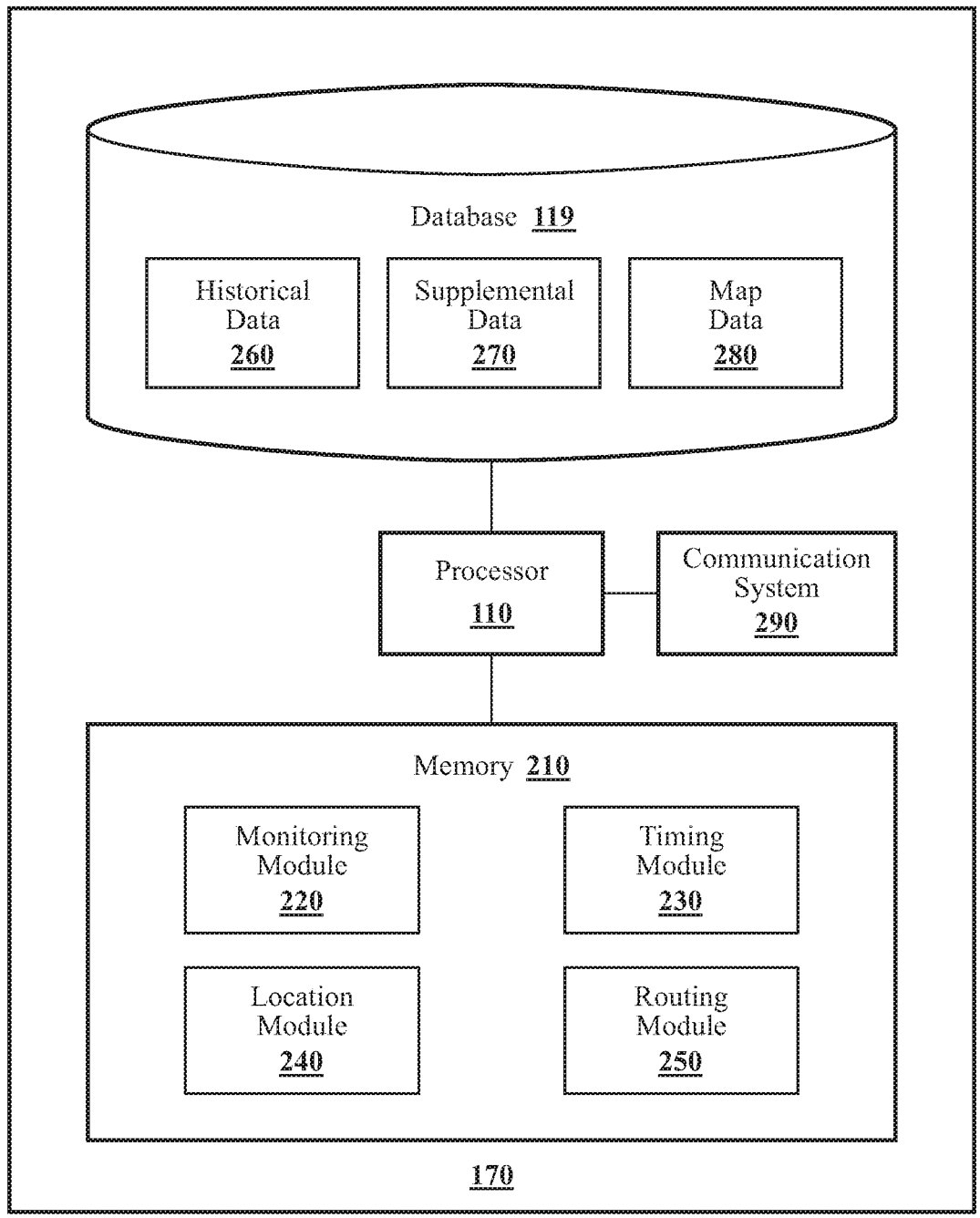
FIG. 2 illustrates one embodiment of a vehicle rest stop recommendation system according to the disclosed subject matter.

With reference to FIG. 2, one embodiment of an implementation of the rest stop recommendation system 170 of FIG. 1 is illustrated. The rest stop recommendation system 170 is shown as including a processor 110 and database 119 from the vehicle 100 of FIG. 1. Accordingly, the processor 110 may be a part of the rest stop recommendation system 170, the rest stop recommendation system 170 may include a processor separate from the processor 110 of the vehicle 100 or the rest stop recommendation system 170 may access the processor 110 through a data bus or another communication path.

The rest stop recommendation system 170 includes a database 119 that stores, among other things, historical data 260 (e.g., indicating past driving behavior), supplemental data 270 (e.g., cluster data indicating driving behavior trends from other drivers), and local map data 280 (e.g., detailed map information that can be drawn from map data 116 in combination with other sources), each of which will be discussed further below. The database 119, in one embodiment, is constructed as an electronic data structure stored in the memory 210 or another data store, such as the vehicle 100 data store 115, a cloud-based storage, a removable memory device, or another suitable location that is accessible to the modules 220, 230, 240 and 250. The database 119 is configured with routines that can be executed by the processor 110 for analyzing stored data, providing stored data, organizing stored data, and so on. Thus, in one embodiment, the database 119 stores data described above (as well as other data) used by the modules 220, 230, 240 and 250 in executing various functions.

Additionally, the rest stop recommendation system 170, in one or more embodiments, includes a memory 210 that stores a monitoring module 220, a timing module 230, a location module 240, and a routing module 250. The memory 210 can be constructed as a random-access memory (RAM), read-only memory (ROM), a hard-disk drive, a flash memory, or other suitable memory for storing the modules 220, 230, 240 and 250.

The rest stop recommendation system 170 can also include a communication system 290 that allows the rest stop recommendation system 170 to transmit/receive data and communicate with, for example, communication networks, server systems, and other systems. The communication system 290 can be implemented as, for example, a wireless communication system including one or more transmitting/receiving devices, one or more transmitting/receiving antennas and a controller for transmitting and receiving data over a wireless network using any of a variety of protocols, such as vehicle-to-everything (V2X), general packet radio service (GPRS), Universal Mobile Telecommunications System (UMTS), Code Division Multiple Access 2000 (CDMA2000), CDMA2000 1x (1xRTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra wideband (UWB), Wibree, and/or any other wireless protocol. In one or more embodiments, the communication system 290 can be configured to receive, for example, supplemental data 270 from one or more external entities, such as a cloud server, edge server, etc.

The modules 220, 230, 240, and 250 are, for example, constructed as computer-readable instructions that when executed by the processor 110 cause the processor 110 to perform the various functions disclosed herein.

The monitoring module 220 is generally constructed including instructions that function to control the processor 110 to monitor, over a period of time, driving behavior of an ego driver and store information indicating the driving behavior as historical data 260.

The timing module 230 is generally constructed including instructions that function to control the processor 110 to determine, based at least in part on the historical data 260, a driver tiredness state, a continuous driving length preference, and a refueling pattern preference, and determine a time to recommend a rest stop based at least in part on the driver tiredness state, the continuous driving length preference, and the refueling pattern preference.

The location module 240 is generally constructed including instructions that function to control the processor 110, at the time to recommend a rest stop, extract from the local map data 280 a plurality of rest stops within a predetermined radius of a position of the vehicle, determine rest stop characteristic preferences based at least in part on the historical data 260, select one or more potential rest stops from among the plurality of rest stops based at least in part on the rest stop characteristic preferences, and present the one or more potential rest stops to the ego driver in a recommendation.

The routing module 250 is generally constructed including instructions that function to control the processor 110 to determine one or more routes, respectively, for the one or more rest recommendations based at least in part on the historical data 260.

The disclosed embodiments can forego using internal sensors and instead use a digital twin framework to determine when to present a rest stop recommendation and to determine the locations of recommended rest stops most likely to meet the ego driver's preferences.

Figure 3:
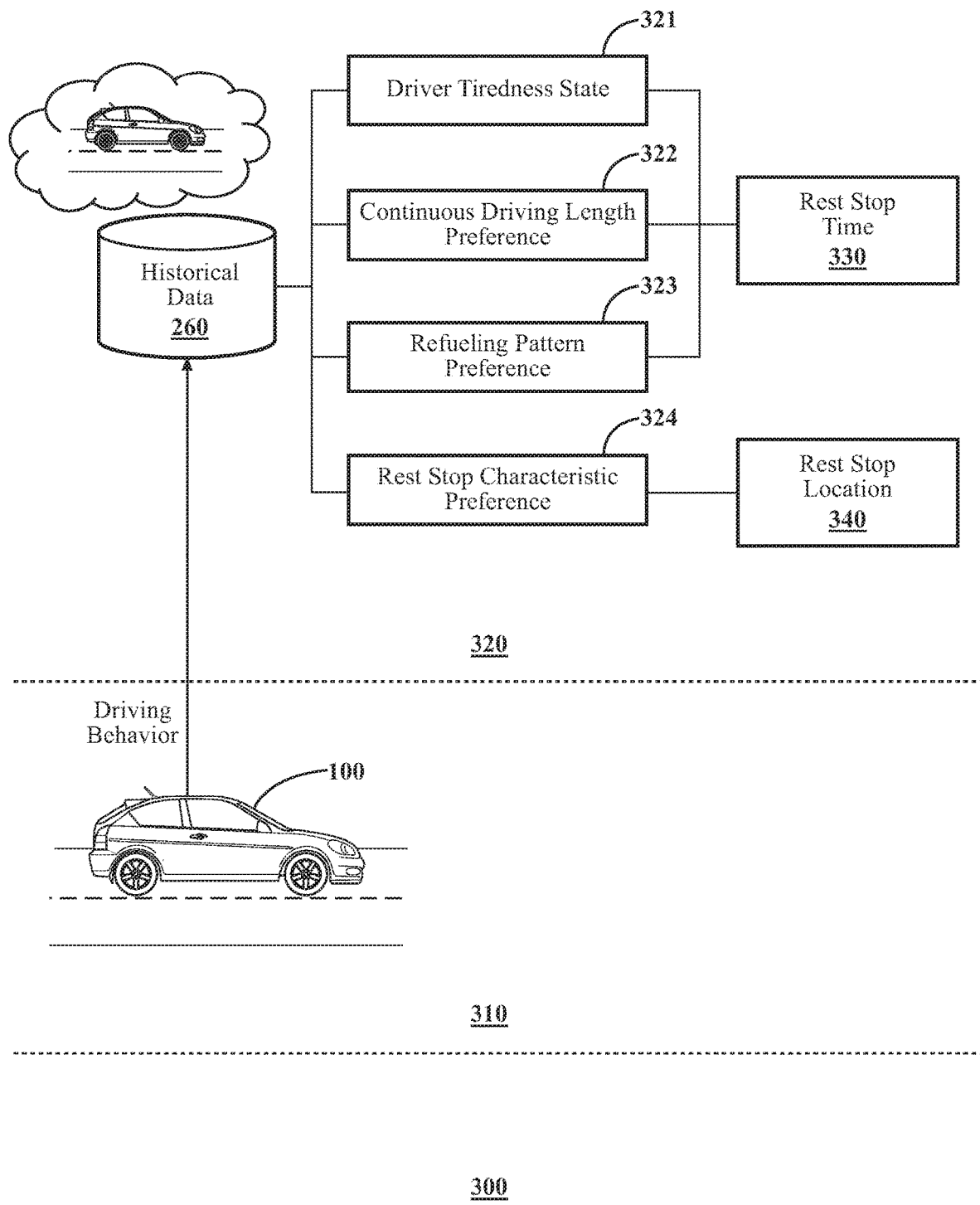
FIG. 3 illustrates an example of a digital twin framework according to the disclosed subject matter.

FIG. 3 shows an example of digital twin framework according to the disclosed embodiments. An ego driver drives the vehicle 100 in the physical world 310. The vehicle 100 (e.g., the rest stop recommendation system 170, monitoring module 220) stores driver behavior over time as historical data 260, forming the digital twin virtual representation 320. The rest stop recommendation system 170 extracts, from the historical data 260, a driver tiredness state 321, a continuous driving length preference 322, a refueling pattern preference 323, and a rest stop characteristic preference 324. The rest stop recommendation system 170 determines a rest stop time 330 based at least in part on the driver tiredness state 321, the continuous driving length preference 322, and the refueling pattern preference 323. The rest stop recommendation system 170 determines a rest stop location 340 based at least in part on the rest stop characteristic preference 324.

Figure 4:
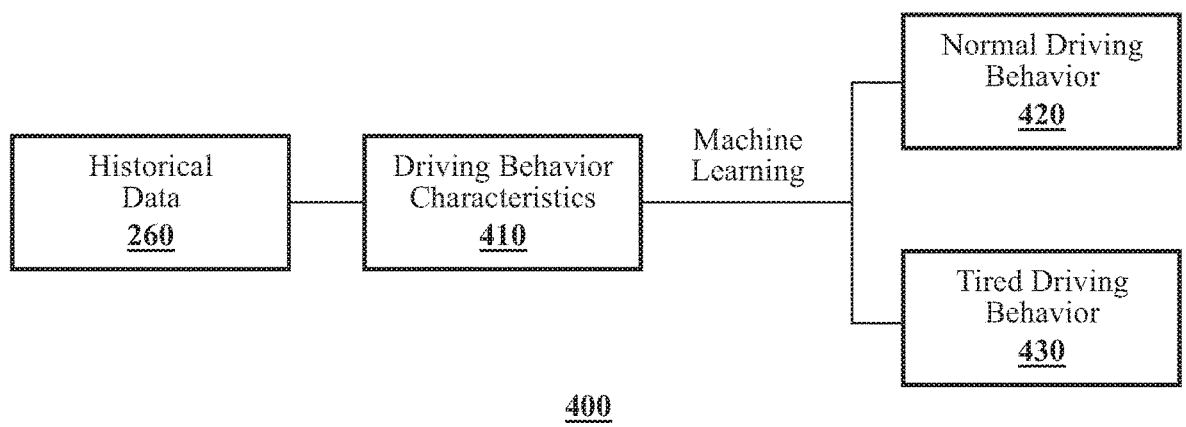
FIG. 4 illustrates an example process the timing module can execute to extract driver behavior patterns from historical data according to the disclosed subject matter.

In one or more embodiments, the rest stop recommendation system 170 (e.g., timing module 230) extracts the driver tiredness state 321 by identifying driver behavior under normal and tired states. FIG. 4 shows an example process 400 the timing module 230 can execute to extract driver behavior patterns from historical data 260. The timing module 230 can determine, based on the historical data 260, past sequences or a matrix to represent driving behavior characteristics 410 (e.g., car-following, lane changing, lane keeping, etc.). The timing module 230 can use a machine learning algorithm (e.g., k-means, hierarchical) to cluster these driving behavior characteristics 410 (sequences or matrices) into two groups, i.e., a normal driving behavior 420 and a tired driving behavior 430.

In one or more embodiments, the timing module 230 can analyze a current driving sequence, e.g., with the machine learning algorithm, to classify the current driving sequence as normal driving behavior 420 or tired driving behavior 430.

Thus, in one or more embodiments the timing module 230 can define driving sequences in the historical data 260, cluster at least a portion of the driving sequences into a normal driving behavior group 420 and a tired driving behavior group 430, process a current driving sequence for cluster classification, and determine the driver tiredness state is 'normal' when the current driving sequence is categorized in the normal driving behavior group 420, or 'tired' when the current driving sequence is categorized in the tired driving behavior group 430.

However, in some cases historical data 260 from a single driver may be lacking or otherwise insufficient to accurately determine a driver tiredness state. Accordingly, in one or more embodiments the timing module 230 can obtain supplemental information to increase accuracy in determining the driving state of the ego driver.

Figure 5:
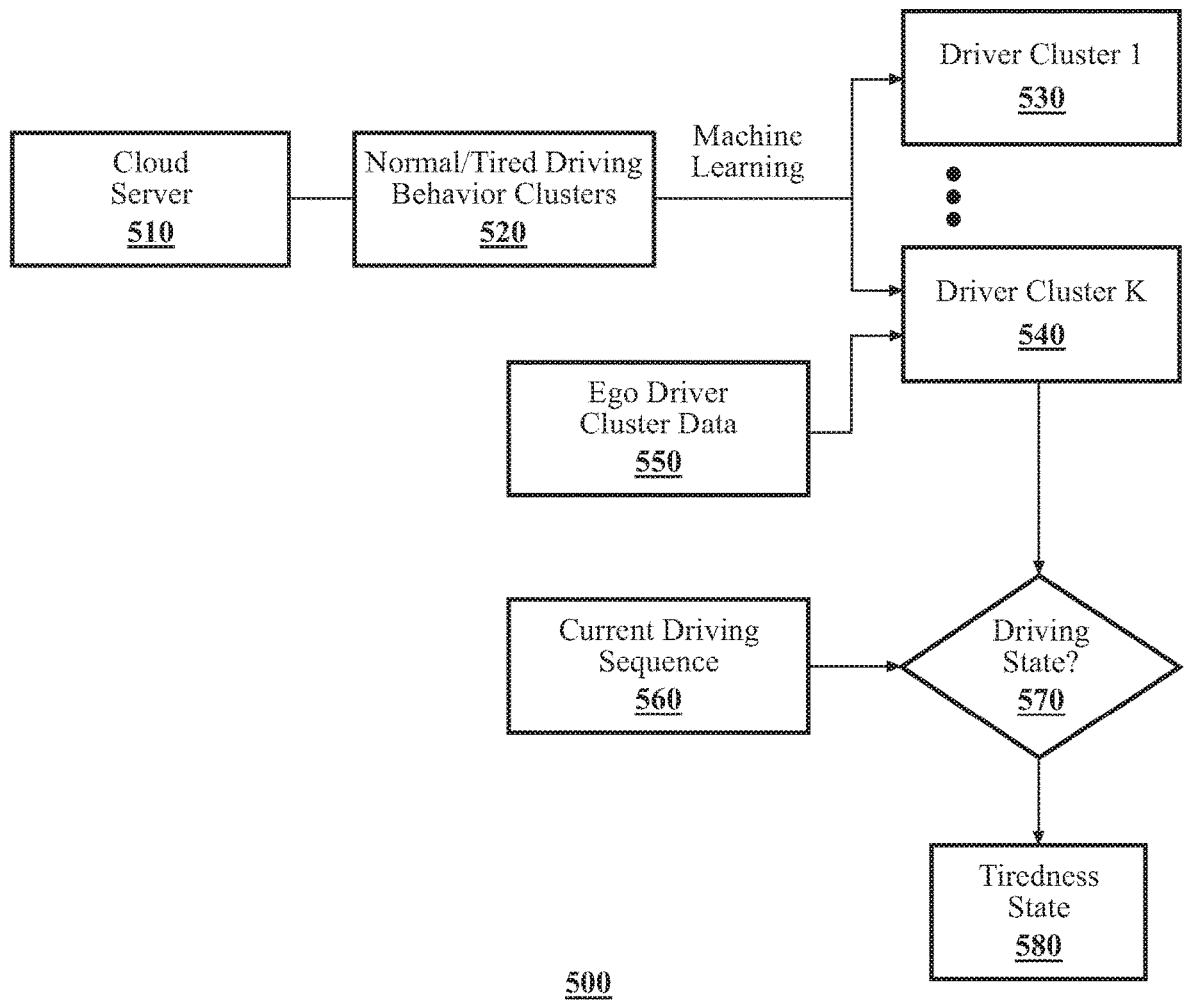
FIG. 5 illustrates an example process the timing module can execute to utilize supplemental driver behavior information and determine a tiredness state of an ego driver according to the disclosed subject matter.

FIG. 5 shows an example process 500 the timing module 230 can execute to utilize supplemental driver behavior information and determine a tiredness state of an ego driver. The rest stop recommendation system 170 can obtain, e.g., from a cloud server 510, normal/tired driver behavior clusters 520 associated with a plurality of participating drivers. The rest stop recommendation system 170 can use a machine learning algorithm to group the participating drivers into two or more clusters 530, 540, etc. Within each cluster, drivers share similar normal/tired driving behaviors. Across clusters, drivers may have different normal/tired driving behaviors.

The rest stop recommendation system 170 can use the machine learning algorithm to determine which cluster the normal/tired driving behavior of the ego driver (e.g., 420, 430 from FIG. 4) should be classified into. For example, the drivers represented in driver cluster K 540 may share similar patterns of normal/tired driving behavior with the ego driver. The rest stop recommendation system 170 can therefore use the normal/tired driving behavior of driver cluster K 540 as supplemental information in determining a tiredness state for the ego driver. For example, rest stop recommendation system 170 can combine the ego driver cluster data 550 with the rest of the data representing normal/tired behavior of drivers in driver cluster K 540. The rest stop recommendation system 170 can then analyze a current driving sequence 560 to determine whether, based on the combined driver cluster K 540 data and ego driver cluster data 550, the current driving sequence 560 indicates a tiredness state 580, e.g., a normal driving state or a tired driving state.

The rest stop recommendation system 170 can execute analysis of the current driving sequence 560 in any of various ways. For example, in one or more embodiments the rest stop recommendation system 170 (e.g., timing module 230) can determine a first similarity value $S_{ck-t}$ between the current driving sequence 560 and the driver cluster K 540 tired behavior and a second similarity value $S_{ck-n}$ between the current driving sequence 560 and the driver cluster K 540 normal behavior. When $S_{ck-n} > S_{ck-t}$, the tiredness state 570 is normal, otherwise, the tiredness state 570 is tired.

Referring back to FIG. 3, the rest stop recommendation system 170 (e.g., timing module 230) can also determine a continuous driving length preference 322 from the historical data 260 by extracting a distribution of lengths of continuous drivetime leading up to a rest stop. In one or more embodiments, the timing module 230 can use a Bayesian Inference approach to capture the uncertainty in a posterior distribution of the lengths of continuous driving time before a rest stop. Accordingly, in one or more embodiments the timing module 230 can use a summation of a mean value and standard deviation value over the distribution and posterior distribution as an estimate of the continuous drivetime length preference 322, or as a threshold length of time to utilize as a factor in determining when the ego driver would prefer to take a rest stop.

Fuel level is another important factor to consider in the recommendation of a rest area, as fuel level can cause range anxiety while driving. The rest stop recommendation system 170 (e.g., timing module 230) can determine a refueling pattern preference 322 from the historical data by extracting a distribution of refueling levels leading up to a rest stop. In one or more embodiments, the timing module 230 can use a Bayesian Inference approach to capture the uncertainty in a posterior distribution of the fuel levels before a rest stop. Accordingly, in one or more embodiments the timing module 230 can use a summation of a mean value and a standard deviation value over the distribution and posterior distribution as an estimate of a refueling level, or as a refueling threshold to utilize as a factor in determining when the ego driver would prefer to stop at a rest stop to refuel.

In summary, rest stop recommendation system 170 considers at least three primary personalized factors to make a determination of rest stop time 330, i.e., determine "when" to present a rest stop recommendation: driver tiredness state 321, continuous driving length preference 322, and refueling pattern preference 323. When the rest stop recommendation system 170 has determined a rest stop time 330 based on one or more of these factors, the system 170 next determines "where" one or more rest areas appropriate for recommendation are located.

Drivers may have different preferences for rest stops, e.g., some drivers may prefer a small town, some drivers may prefer a conventional rest area, some drivers may find a detour acceptable while some drivers may prefer the closest rest area. Furthermore, drivers may prefer rest areas with specific restaurants, gas stations or convenience stores. Accordingly, the rest stop recommendation system 170 can determine rest area preferences for the ego driver in order to select appropriate rest areas to recommend.

In one or more embodiments, the rest stop recommendation system 170 can extract rest area characteristics (e.g., gas stations, restaurants, town or conventional area, distance from highway, etc.) of previously visited rest areas from the historical data 260 and select one or more potential rest areas to present to the ego driver based at least in part on the extracted characteristics.

Figure 6:
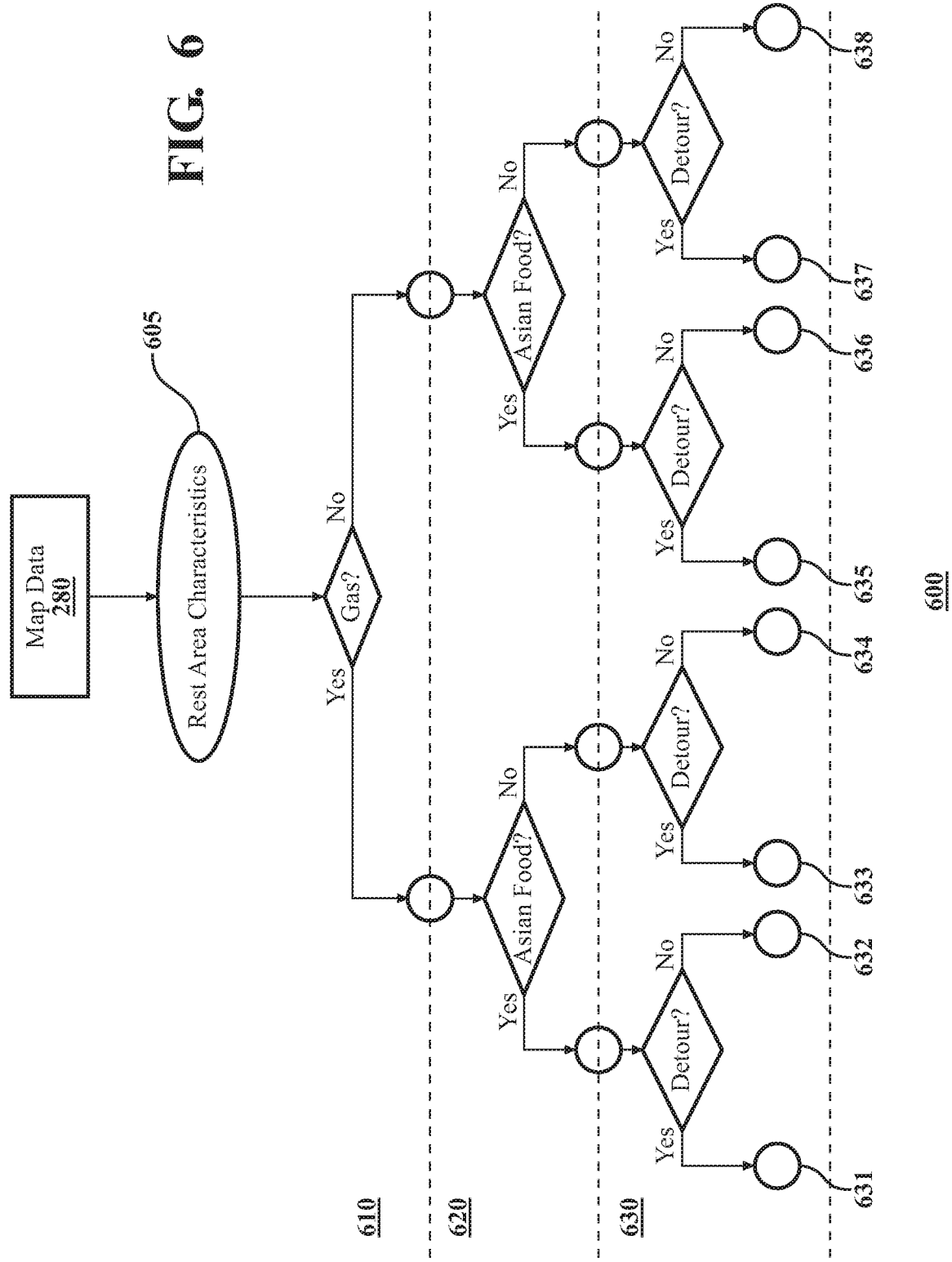
FIG. 6 illustrates an example decision tree according to the disclosed subject matter.

For example, in one or more embodiments the rest stop recommendation system 170 (e.g., location module 240) can train a personalized, hierarchical decision tree model to weigh potential rest areas and determine most suitable recommendations. FIG. 6 shows an example decision tree 600 according to the disclosed embodiments. In one or more embodiments, the location module 240 can determine, based on historical data 260, that a first rest area characteristic appears most frequently in rest areas that the ego driver has stopped at in the past and rank the first characteristic as a first tier decision. For example, in the decision tree 600 the first-tier 610 characteristic is the availability of gas at the rest area.

The location module 240 can proceed to rank subsequent characteristics to build out the decision tree 600 in order of importance, for example, based on frequency of occurrence or manual input from the ego driver. For example, in one or more embodiments the rest stop recommendation system 170 can provide an interface, e.g., via a user interface of the vehicle 100, through which the ego driver can directly input and rank preferred characteristics. In either case regardless of how the importance ranking is determined, the location module 240 can construct the decision tree 600 hierarchically ranking various area characteristics. In the example decision tree 600, the second-tier 620 characteristic is the presence of a restaurant that serves Asian food, the third-tier characteristic 630 is whether the rest stop requires a detour, and so on.

Accordingly, the decision tree 600 can receive characteristics of a rest area as input and output a rating for the rest area. For example, each result (e.g., 631-638) in the final layer (e.g., 630) of the decision tree 600 can be assigned a rating. Figuratively speaking, the ratings further to the left result in meeting more characteristic preference and could be assigned relatively higher ratings.

When the rest stop recommendation system 170 (e.g., timing module 230) determines a rest time, the location module 240 can extract, from the local map data 280, rest area characteristics 605 of one or more potential rest areas within a T drive-time or distance radius of a current location of the vehicle 100. The local map data 280 can be extracted from stored map data 116 (FIG. 1), obtained from an online map service provider, stored locally, retrieved from other sources or a combination thereof. The timing module 230 can input the rest area characteristics 605 into the decision tree 600 and receive a rating for each potential rest area. The timing module 230 can select a one or more of the highest rated potential rest areas to present as the rest stop location(s) 340 (FIG. 3) to recommend for a rest stop.

In one or more embodiments, the routing module 250 can determine one or more personalized routes, respectively, for the one or more rest stop recommendations based at least in part on the historical data 260. For example, if the recommended rest stop locations lack a particular rest area characteristic preference (e.g., favorite restaurant X), the routing module 250 can attempt to determine a route that will pass by a point of interest that contains the missing rest area characteristic preference (e.g., attempt to create a personalized route that passed by favorite restaurant X).

Accordingly, the disclosed rest stop recommendation system 170 can identify normal and tired driving behavior using historical data 260 instead of in-cabin sensors and utilize clustering and machine learning based on the historical data 260 to predict in real-time a tiredness state 321 of the ego driver. The disclosed rest stop recommendation system 170 can further determine an ego driver's personalized continuous driving length preference 322 and refueling pattern preference 323 from the historical data 260. Based on one or more of the tiredness state 321, the continuous driving length preference 322, and the refueling pattern preference 323, the disclosed rest stop recommendation system 170 can determine a rest stop time 330, i.e., "when" to present a rest stop recommendation.

Furthermore, the disclosed rest stop recommendation system 170 can determine the ego driver's rest area characteristic preferences, identify one or more potential rest stops within a radius of the current location of the vehicle 100, select the potential rest stops that best meet the ego driver's rest area characteristic preferences and present personalized routes to the potential rest stops for the ego driver to select.

Figure 7:
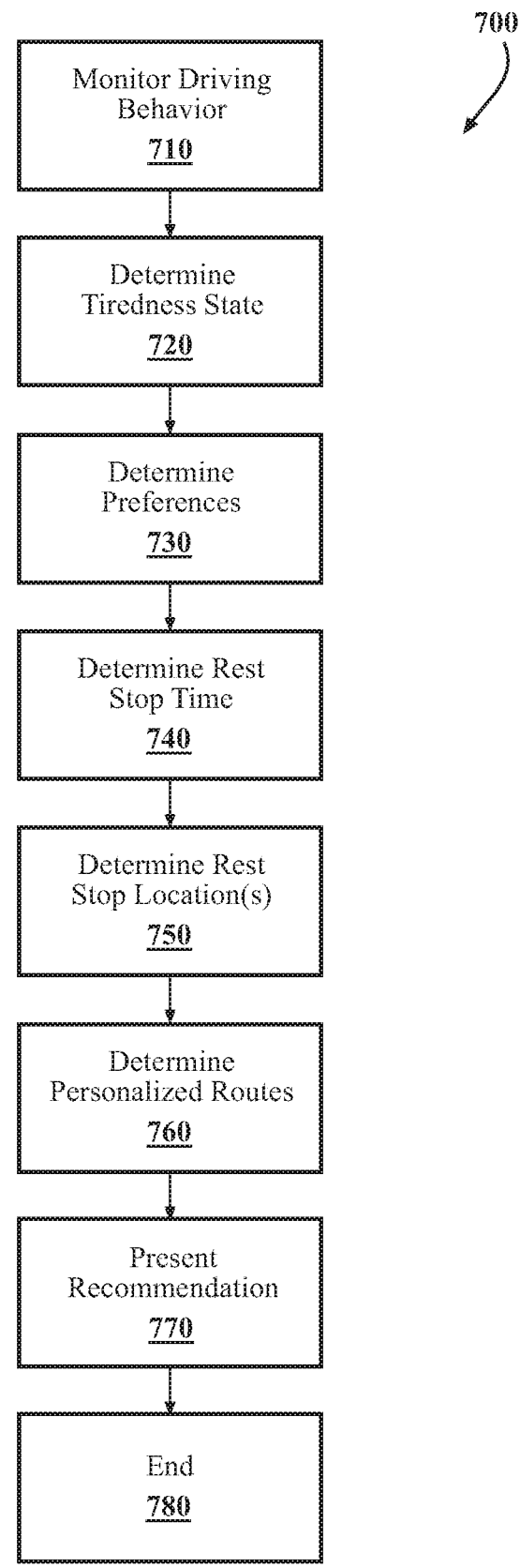
FIG. 7 illustrates a flowchart of a method of determining a rest stop recommendation according to the disclosed subject matter.

Additional and optional features of the rest stop recommendation system 170 will now be discussed. FIG. 7 illustrates a flowchart of a method 700 of determining a rest stop recommendation according to the disclosed embodiments. Method 700 will be discussed from the perspective of the rest stop recommendation system 170 of FIGS. 1-6. While method 700 is discussed in combination with the rest stop recommendation system 170, it should be appreciated that the method 700 is also not limited to being implemented within the rest stop recommendation system 170 but is instead one example of a system that may implement the method 700.

At operation 710, the rest stop recommendation system 170 (e.g., monitoring module 220) monitors, over a period of time, driving behavior of an ego driver and store information indicating the driving behavior as historical data 260. In one or more embodiments the driving behavior can include, for example and without limitation: acceleration/deceleration rate, velocity, steering adjustments, lane changes, swerves, distance following preceding car, turning speed, lane drift, length of continuous driving, stops, stop locations, length of time at a stop, and speed relative to posted speed limit.

In one or more embodiments the monitoring module 220 can store metadata associated with the historical data 260. The metadata can include, for example and without limitation, timestamp data and geolocation data (e.g., GPS coordinates), either of which can be used to define fixed length (i.e., time or distance) driving sequences based on the monitored driving behavior. In one or more embodiments, the monitoring module 220 stores the driving behavior and associated metadata as historical data 260 in the database 119.

At operation 720, the rest stop recommendation system 170 (e.g., timing module 230) determines, based at least in part on the historical data 260, a driver tiredness state 321. For example, the timing module 230 can define driving sequences in the historical data 260, cluster at least a portion of the driving sequences into a normal driving behavior group and a tired driving behavior group, process a current driving sequence for cluster classification, and determine the driver tiredness state is 'normal' when the current driving sequence is classified in the normal driving behavior group 420, or 'tired' when the current driving sequence is classified in the tired driving behavior group 430.

In one or more embodiments, the timing module 230 can obtain supplemental cluster data indicating normal/tired driving clusters for a plurality of drivers, cluster the plurality of drivers into similarity behavior groups, select a similarity behavior group for the ego driver, and supplement the normal driver behavior group 420 and the tired driving behavior group 430 based on the normal/tired driving clusters of drivers in the similarity behavior group At operation 730, the timing module 230 can determine one or more rest-stop preferences, such as a continuous driving length preference 322 and a refueling pattern preference 323. For example, in one or more embodiments, the timing module 230 can determine a continuous driving length preference 322 by extracting, from the historical data 260, a distribution of sequences of continuous drive time lengths before a rest, determining a posterior distribution of continuous driving time lengths before a rest based on Bayesian inference, and determining the continuous driving length preference as a summation of a mean value and standard deviation value over the distribution and the posterior distribution.

In one or more embodiments, the timing module 230 can determine a refueling pattern preference 323 by extracting, from the historical data, a distribution of fuel level amounts before refueling, determining a posterior distribution of fuel level amounts before refueling based on Bayesian inference, and determining the refueling pattern preference as a summation of a mean value and standard deviation value over the distribution and the posterior distribution.

At operation 740, the timing module 230 can determine a time to recommend a rest stop (i.e., a rest stop time 330) based on one or more of the driver tiredness state 321, the continuous driving length preference 322 and the refueling pattern preference 323.

At operation 750, the rest stop recommendation system 170 (e.g., location module 240) determines one or more rest stop locations 340. In one or more embodiments, the location module 240 determines the rest stop locations 340 by extracting, from a map database, a plurality of rest stops within a predetermined radius of a position of the vehicle, determining rest stop characteristic preferences based at least in part on the historical data 260, and selecting one or more potential rest stops from among the plurality of rest stops based at least in part on the rest stop characteristic preferences.

At operation 760, the rest stop recommendation system 170 (e.g., routing module 250) determines one or more routes, respectively, for the one or more rest stop recommendations based at least in part on the historical data 260.

At operation 770, the rest stop recommendation system 170 presents one or more recommended rest stop locations with associated personalized routes to the ego driver for selection. The process ends at operation 780. Thus, the disclosed the rest stop recommendation system 170 can determine when to present recommendations for a rest stop as well as provide personalized rest stop recommendation options and personalized routes to the recommended rest stops.

FIG. 1, which shows various components of the vehicle 100, will now be discussed in full detail as an example environment within which the system and methods disclosed herein may operate.

In one or more embodiments, the vehicle 100 is an autonomous vehicle. As used herein, "autonomous vehicle" refers to a vehicle that operates in an autonomous mode. "Autonomous mode" refers to navigating and/or maneuvering the vehicle 100 along a travel route using one or more computing systems to control the vehicle 100 with minimal or no input from a human driver. In one or more embodiments, the vehicle 100 is highly automated or completely automated. In one embodiment, the vehicle 100 is configured with one or more semi-autonomous operational modes in which one or more computing systems perform a portion of the navigation and/or maneuvering of the vehicle along a travel route, and a vehicle operator (i.e., ego driver) provides inputs to the vehicle 100 to perform a portion of the navigation and/or maneuvering of the vehicle 100 along a travel route.

In some instances, the vehicle 100 is configured to switch selectively between an autonomous mode, one or more semi-autonomous operational modes, and/or a manual mode. Such switching can be implemented in a suitable manner, now known or later developed. "Manual mode" means that all or a majority of the navigation and/or maneuvering of the vehicle is performed according to inputs received from a user (e.g., human driver). In one or more arrangements, the vehicle 100 can be a conventional vehicle that is configured to operate in only a manual mode.

The vehicle 100 can include one or more processors 110. In one or more arrangements, the processor(s) 110 can be a main processor of the vehicle 100. For instance, the processor(s) 110 can be an electronic control unit (ECU). The vehicle 100 can include one or more data stores 115 for storing one or more types of data. The data store 115 can include volatile and/or non-volatile memory. Examples of suitable data stores 115 include RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The data store 115 can be a component of the processor(s) 110, or the data store 115 can be operatively connected to the processor(s) 110 for use thereby. The term "operatively connected," as used throughout this description, can include direct or indirect connections, including connections without direct physical contact.

In one or more arrangements, the one or more data stores 115 can implement the database 119 (FIG. 2) and can further include map data 116. The map data 116 can include maps of one or more geographic areas. In some instances, the map data 116 can include information or data on roads, traffic control devices, road markings, structures, features, and/or landmarks in the one or more geographic areas. The map data 116 can be in any suitable form. In some instances, the map data 116 can include aerial views of an area. In some instances, the map data 116 can include ground views of an area, including 360-degree ground views. The map data 116 can include measurements, dimensions, distances, and/or information for one or more items included in the map data 116 and/or relative to other items included in the map data 116. The map data 116 can include a digital map with information about road geometry. The map data 116 can be high quality and/or highly detailed.

In one or more arrangements, the map data 116 can include one or more terrain maps 117. The terrain map(s) 117 can include information about the ground, terrain, roads, surfaces, and/or other features of one or more geographic areas. The terrain map(s) 117 can include elevation data in the one or more geographic areas. The map data 116 can be high quality and/or highly detailed. The terrain map(s) 117 can define one or more ground surfaces, which can include paved roads, unpaved roads, land, and other things that define a ground surface.

In one or more arrangements, the map data 116 can include one or more static obstacle maps 118. The static obstacle map(s) 118 can include information about one or more static obstacles located within one or more geographic areas. A "static obstacle" is a physical object whose position does not change or substantially change over a period of time and/or whose size does not change or substantially change over a period of time. Examples of static obstacles include trees, buildings, curbs, fences, railings, medians, utility poles, statues, monuments, signs, benches, furniture, mailboxes, large rocks, hills. The static obstacles can be objects that extend above ground level. The one or more static obstacles included in the static obstacle map(s) 118 can have location data, size data, dimension data, material data, and/or other data associated with it. The static obstacle map(s) 118 can include measurements, dimensions, distances, and/or information for one or more static obstacles. The static obstacle map(s) 118 can be high quality and/or highly detailed. The static obstacle map(s) 118 can be updated to reflect changes within a mapped area.

As noted above, the vehicle 100 can include the sensor system 120. The sensor system 120 can include one or more sensors. "Sensor" means any device, component and/or system that can detect, and/or sense something. The one or more sensors can be configured to detect, and/or sense in real-time. As used herein, the term "real-time" means a level of processing responsiveness that a user or system senses as sufficiently immediate for a particular process or determination to be made, or that enables the processor to keep up with some external process.

In arrangements in which the sensor system 120 includes a plurality of sensors, the sensors can work independently from each other. Alternatively, two or more of the sensors can work in combination with each other. In such case, the two or more sensors can form a sensor network. The sensor system 120 and/or the one or more sensors can be operatively connected to the processor(s) 110, the data store(s) 115, and/or another element of the vehicle 100 (including any of the elements shown in FIG. 1). The sensor system 120 can acquire data of at least a portion of the external environment of the vehicle 100 (e.g., nearby vehicles).

The sensor system 120 can include any suitable type of sensor. Various examples of different types of sensors will be described herein. However, it will be understood that the embodiments are not limited to the particular sensors described. The sensor system 120 can include one or more vehicle sensors 121. The vehicle sensor(s) 121 can detect, determine, and/or sense information about the vehicle 100 itself, such as one or more actual states of the vehicle 100. In one or more arrangements, the vehicle sensor(s) 121 can be configured to detect, and/or sense position and orientation changes of the vehicle 100, such as, for example, based on inertial acceleration. In one or more arrangements, the vehicle sensor(s) 121 can include one or more accelerometers, one or more gyroscopes, an inertial measurement unit (IMU), a dead-reckoning system, a global navigation satellite system (GNSS), a global positioning system (GPS), a navigation system 147, and/or other suitable sensors. The vehicle sensor(s) 121 can be configured to detect, and/or sense one or more characteristics of the vehicle 100. In one or more arrangements, the vehicle sensor(s) 121 can include a speedometer to determine a current speed of the vehicle 100.

Alternatively, or in addition, the sensor system 120 can include one or more environment sensors 122 configured to acquire, and/or sense driving environment data. "Driving environment data" includes data or information about the external environment in which an autonomous vehicle is located or one or more portions thereof. For example, the one or more environment sensors 122 can be configured to detect, quantify and/or sense obstacles in at least a portion of the external environment of the vehicle 100 and/or information/data about such obstacles. Such obstacles may be stationary objects and/or dynamic objects. The one or more environment sensors 122 can be configured to detect, measure, quantify and/or sense other things in the external environment of the vehicle 100, such as, for example, lane markers, signs, traffic lights, traffic signs, lane lines, crosswalks, curbs proximate the vehicle 100, off-road objects, etc.

Various examples of sensors of the sensor system 120 will be described herein. The example sensors may be part of the one or more environment sensors 122 and/or the one or more vehicle sensors 121. However, it will be understood that the embodiments are not limited to the particular sensors described.

As an example, in one or more arrangements, the sensor system 120 can include one or more RADAR sensors 123, one or more LIDAR sensors 124, one or more sonar sensors 125, and/or one or more cameras 126, e.g, one or more monocular cameras. In one or more arrangements, the one or more cameras 126 can be high dynamic range (HDR) cameras or infrared (IR) cameras.

The vehicle 100 can include an input system 130. An "input system" includes any device, component, system, element or arrangement or groups thereof that enable information/data to be entered into a machine. The input system 130 can receive an input from a vehicle passenger (e.g., a driver or a passenger), such as, for example, rest area characteristics preferences.

The vehicle 100 can include an output system 135. An "output system" includes any device, component, or arrangement or groups thereof that enable information/data to be presented to a vehicle passenger (e.g., a person, a vehicle passenger, etc.). The output system 135 can function as part of an interface that can present, for example, forecast notifications as described above.

The vehicle 100 can include one or more vehicle systems 140. Various examples of the one or more vehicle systems 140 are shown in FIG. 1. However, the vehicle 100 can include more, fewer, or different vehicle systems. It should be appreciated that although particular vehicle systems are separately defined, each or any of the systems or portions thereof may be otherwise combined or segregated via hardware and/or software within the vehicle 100. The vehicle 100 can include a propulsion system 141, a braking system 142, a steering system 143, throttle system 144, a transmission system 145, a signaling system 146, and/or a navigation system 147. Each of these systems can include one or more devices, components, and/or a combination thereof, now known or later developed. One or more of these systems can by operably connected to wheels of the vehicle in a manner that allows individual application of control or commands implemented by the respective system.

The navigation system 147 can include one or more devices, applications, and/or combinations thereof, now known or later developed, configured to determine the geographic location of the vehicle 100 and/or to determine a travel route for the vehicle 100. The navigation system 147 can include one or more mapping applications to determine a travel route for the vehicle 100. The navigation system 147 can include a global positioning system, a local positioning system or a geolocation system.

The processor(s) 110 and/or the autonomous driving module(s) 160 can be operatively connected to communicate with the various vehicle systems 140 and/or individual components thereof. For example, returning to FIG. 1, the processor(s) 110 and/or the autonomous driving module(s) 160 can be in communication to send and/or receive information from the various vehicle systems 140 to control the movement, speed, maneuvering, heading, direction, etc. of the vehicle 100. The processor(s) 110 and/or the autonomous driving module(s) 160 may control some or all of these vehicle systems 140 and, thus, may be partially or fully autonomous.

The processor(s) 110 and/or the autonomous driving module(s) 160 may be operable to control the navigation and/or maneuvering of the vehicle 100 by controlling one or more of the vehicle systems 140 and/or components thereof. For instance, when operating in an autonomous mode, the processor(s) 110 and/or the autonomous driving module(s) 160 can control the direction and/or speed of the vehicle 100. The processor(s) 110 and/or the autonomous driving module(s) 160 can cause the vehicle 100 to accelerate (e.g., by increasing the supply of fuel provided to the engine), decelerate (e.g., by decreasing the supply of fuel to the engine and/or by applying brakes) and/or change direction (e.g., by turning the front two wheels). As used herein, "cause" or "causing" means to make, force, compel, direct, command, instruct, and/or enable an event or action to occur or at least be in a state where such event or action may occur, either in a direct or indirect manner.

The vehicle 100 can include one or more actuator(s) 150. The actuator(s) 150 can be any element or combination of elements operable to modify, adjust and/or alter one or more of the vehicle systems 140 or components thereof to responsive to receiving signals or other inputs from the processor(s) 110 and/or the autonomous driving module(s) 160. Any suitable actuator can be used. For instance, the one or more actuators 150 can include motors, pneumatic actuators, hydraulic pistons, relays, solenoids, and/or piezoelectric actuators, just to name a few possibilities.

The vehicle 100 can include one or more modules, at least some of which are described herein. The modules can be implemented as computer-readable program code that, when executed by a processor 110, implement one or more of the various processes described herein. One or more of the modules can be a component of the processor(s) 110, or one or more of the modules can be executed on and/or distributed among other processing systems to which the processor(s) 110 is operatively connected. The modules can include instructions (e.g., program logic) executable by one or more processor(s) 110. Alternatively, or in addition, one or more data store 115 may contain such instructions.

In one or more arrangements, one or more of the modules described herein can include artificial or computational intelligence elements, e.g., neural network, fuzzy logic or other machine learning algorithms. Further, in one or more arrangements, one or more of the modules can be distributed among a plurality of the modules described herein. In one or more arrangements, two or more of the modules described herein can be combined into a single module.

The vehicle 100 can include one or more autonomous driving modules 160. The autonomous driving module(s) 160 can be configured to receive data from the sensor system 120 and/or any other type of system capable of capturing information relating to the vehicle 100 and/or the external environment of the vehicle 100. In one or more arrangements, the autonomous driving module(s) 160 can use such data to generate one or more driving scene models. The autonomous driving module(s) 160 can determine position and velocity of the vehicle 100. The autonomous driving module(s) 160 can determine the location of obstacles, obstacles, or other environmental features including traffic signs, trees, shrubs, neighboring vehicles, pedestrians, etc.

The autonomous driving module(s) 160 can be configured to receive, and/or determine location information for obstacles within the external environment of the vehicle 100 for use by the processor(s) 110, and/or one or more of the modules described herein to estimate position and orientation of the vehicle 100, vehicle position in global coordinates based on signals from a plurality of satellites, or any other data and/or signals that could be used to determine the current state of the vehicle 100 or determine the position of the vehicle 100 with respect to its environment for use in either creating a map or determining the position of the vehicle 100 in respect to map data.

The autonomous driving module(s) 160 can be configured to determine travel path(s) and determine current autonomous driving maneuvers for the vehicle 100, future autonomous driving maneuvers and/or modifications to current autonomous driving maneuvers based on data acquired by the sensor system 120, driving scene models, and/or data from any other suitable source. "Driving maneuver" means one or more actions that affect the movement of a vehicle. Examples of driving maneuvers include: accelerating, decelerating, braking, turning, moving in a lateral direction of the vehicle 100, changing travel lanes, merging into a travel lane, and/or reversing, just to name a few possibilities. The autonomous driving module(s) 160 can be configured can be configured to implement determined driving maneuvers. The autonomous driving module(s) 160 can cause, directly or indirectly, such autonomous driving maneuvers to be implemented. As used herein, "cause" or "causing" means to make, command, instruct, and/or enable an event or action to occur or at least be in a state where such event or action may occur, either in a direct or indirect manner. The autonomous driving module(s) 160 can be configured to execute various vehicle functions and/or to transmit data to, receive data from, interact with, and/or control the vehicle 100 or one or more systems thereof (e.g., one or more of vehicle systems 140).

Detailed embodiments are disclosed herein. However, it is to be understood that the disclosed embodiments are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in FIGS. 1-6, but the embodiments are not limited to the illustrated structure or application.

The flowcharts and block diagrams in the figures illustrate the architecture, functionality, and operation of possible implementations of systems, methods, and computer program products according to various embodiments. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

The systems, components and/or processes described above can be realized in hardware or a combination of hardware and software and can be realized in a centralized fashion in one processing system or in a distributed fashion where different elements are spread across several interconnected processing systems. Any kind of processing system or another apparatus adapted for carrying out the methods described herein is suited. A typical combination of hardware and software can be a processing system with computer-usable program code that, when being loaded and executed, controls the processing system such that it carries out the methods described herein. The systems, components and/or processes also can be embedded in a computer-readable storage, such as a computer program product or other data programs storage device, readable by a machine, tangibly embodying a program of instructions executable by the machine to perform methods and processes described herein. These elements also can be embedded in an application product which comprises all the features enabling the implementation of the methods described herein and, which when loaded in a processing system, is able to carry out these methods.

Furthermore, arrangements described herein may take the form of a computer program product embodied in one or more computer-readable media having computer-readable program code embodied, e.g., stored, thereon. Any combination of one or more computer-readable media may be utilized. The computer-readable medium may be a computer-readable signal medium or a computer-readable storage medium. The phrase "computer-readable storage medium" means a non-transitory storage medium. A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: a portable computer diskette, a hard disk drive (HDD), a solid-state drive (SSD), a read-only memory (ROM), an erasable programmable read-only memory (EPROM or Flash memory), a portable compact disc read-only memory (CD-ROM), a digital versatile disc (DVD), an optical storage device, a magnetic storage device, or any suitable combination of the foregoing. In the context of this document, a computer-readable storage medium may be any tangible medium that can contain, or store a program for use by or in connection with an instruction execution system, apparatus, or device.

Generally, modules as used herein include routines, programs, objects, components, data structures, and so on that perform particular tasks or implement particular data types. In further aspects, a memory generally stores the noted modules. The memory associated with a module may be a buffer or cache embedded within a processor, a RAM, a ROM, a flash memory, or another suitable electronic storage medium. In still further aspects, a module as envisioned by the present disclosure is implemented as an application-specific integrated circuit (ASIC), a hardware component of a system on a chip (SoC), as a programmable logic array (PLA), or as another suitable hardware component that is embedded with a defined configuration set (e.g., instructions) for performing the disclosed functions.

Program code embodied on a computer-readable medium may be transmitted using any appropriate medium, including but not limited to wireless, wireline, optical fiber, cable, RF, etc., or any suitable combination of the foregoing. Computer program code for carrying out operations for aspects of the present arrangements may be written in any combination of one or more programming languages, including an object-oriented programming language such as Java™ Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The phrase "at least one of . . . and . . . " as used herein refers to and encompasses any and all possible combinations of one or more of the associated listed items. As an example, the phrase "at least one of A, B, and C" includes A only, B only, C only, or any combination thereof (e.g., AB, AC, BC or ABC).

Aspects herein can be embodied in other forms without departing from the spirit or essential attributes thereof. Accordingly, reference should be made to the following claims, rather than to the foregoing specification, as indicating the scope hereof.

What is claimed is:

1. A vehicle having a rest stop recommendation system for the vehicle, comprising:
    at least one vehicle system, wherein the at least one vehicle system comprises at least one of a propulsion system, a braking system, a steering system, a throttle system, a transmission system, a signaling system, or a navigation system;
    a map database;
    one or more processors;
    a memory communicably coupled to the one or more processors and storing:
        a monitoring module including instructions that when executed by the one or more processors cause the one or more processors to monitor, over a period of time, driving behavior of an ego driver and store information indicating the driving behavior as historical data;
        a timing module including instructions that when executed by the one or more processors cause the one or more processors to determine, based at least in part on the historical data, a driver tiredness state, a continuous driving length preference, and a refueling pattern preference, and determine a time to recommend a rest stop based at least in part on the driver tiredness state, the continuous driving length preference, and the refueling pattern preference, wherein the instructions to determine the continuous driving length preference:
            extract, from the historical data, a distribution of sequences of continuous drive time lengths before a rest;
            determine a posterior distribution of the continuous drive time lengths before the rest based on Bayesian inference; and
            determine the continuous driving length preference as a summation of a mean value and a standard deviation value over the distribution and the posterior distribution;
        a location module including instructions that when executed by the one or more processors cause the one or more processors to extract, at the time to recommend the rest stop and from the map database, a plurality of rest stops within a predetermined radius of a position of the vehicle, determine rest stop characteristic preferences based at least in part on the historical data, select one or more potential rest stops from among the plurality of rest stops based at least in part on the rest stop characteristic preferences, and present the one or more potential rest stops to the ego driver in a recommendation; and
        a routing module including instructions that when executed by the one or more processors cause the one or more processors to determine one or more routes, respectively, for the one or more potential rest stops based at least in part on the historical data;
    an input system configured to receive a selection of a route of the one or more routes; and
    an autonomous driving module communicably coupled to the one or more processors, the input system, and the at least one vehicle system, and configured to communicate with the at least one vehicle system to perform, in an automated manner, at least a portion of a navigation of the vehicle along the route.

2. The rest stop recommendation system of claim 1, wherein the timing module includes instructions to determine the driver tiredness state by:
    defining driving sequences in the historical data;
    clustering at least a portion of the driving sequences into a normal driving behavior group and a tired driving behavior group;
    processing a current driving sequence for cluster classification; and
    determining the driver tiredness state is 'normal' when the current driving sequence is classified in the normal driving behavior group, or 'tired' when the current driving sequence is classified in the tired driving behavior group.

3. The rest stop recommendation system of claim 2, wherein the timing module further includes instructions to, prior to processing the current driving sequence for cluster classification:
    obtain supplemental cluster data indicating normal/tired driving clusters for a plurality of drivers;
    cluster the plurality of drivers into similarity behavior groups;
    select a similarity behavior group for the ego driver; and
    supplement the normal driving behavior group and the tired driving behavior group based on the normal/tired driving clusters of drivers in the similarity behavior group.

4. The rest stop recommendation system of claim 1, wherein the timing module includes instructions to determine the refueling pattern preference by:
    extracting, from the historical data, a distribution of fuel level amounts before refueling;

determining a posterior distribution of the fuel level amounts before refueling based on Bayesian inference; and determining the refueling pattern preference as a summation of a mean value and a standard deviation value over the distribution and the posterior distribution.

5. The rest stop recommendation system of claim 1, wherein the rest stop characteristic preferences include one or more of:
- a detour distance traveled to the rest stop;
- a type of restaurant located at the rest stop; or
- a presence of a gas station at the rest stop.

6. A method of determining and providing a rest stop recommendation, comprising:
- monitoring, over a period of time, driving behavior of an ego driver driving a vehicle and store information indicating the driving behavior as historical data;
- determining, based at least in part on the historical data, a driver tiredness state, a continuous driving length preference, and a refueling pattern preference, wherein the determining the continuous driving length preference comprises:
  - extracting, from the historical data, a distribution of sequences of continuous drive time lengths before a rest;
  - determining a posterior distribution of the continuous drive time lengths before the rest based on Bayesian inference; and
  - determining the continuous driving length preference as a summation of a mean value and a standard deviation value over the distribution and the posterior distribution;
- determining a time to recommend a rest stop based at least in part on the driver tiredness state, the continuous driving length preference, and the refueling pattern preference;
- extracting, from a map database, a plurality of rest stops within a predetermined radius of a position of the vehicle;
- determining rest stop characteristic preferences based at least in part on the historical data;
- selecting one or more potential rest stops from among the plurality of rest stops based at least in part on the rest stop characteristic preferences;
- presenting the one or more potential rest stops to the ego driver in a recommendation;
- determining one or more routes, respectively, for the one or more potential rest stops based at least in part on the historical data;
- receiving, via an input system, a selection of a route of the one or more routes; and
- communicating with at least one vehicle system to perform, in an automated manner, at least a portion of a navigation of the vehicle along the route,
- wherein the at least one vehicle system comprises at least one of a propulsion system, a braking system, a steering system, a throttle system, a transmission system, a signaling system, or a navigation system.

7. The method of claim 6, wherein the determining the driver tiredness state comprises:
- defining driving sequences in the historical data;
- clustering at least a portion of the driving sequences into a normal driving behavior group and a tired driving behavior group;
- processing a current driving sequence for cluster classification; and
- determining the driver tiredness state is 'normal' when the current driving sequence is classified in the normal driving behavior group, or 'tired' when the current driving sequence is classified in the tired driving behavior group.

8. The method of claim 7, further comprising, prior to processing the current driving sequence for cluster classification:
- obtaining supplemental cluster data indicating normal/tired driving clusters for a plurality of drivers;
- clustering the plurality of drivers into similarity behavior groups;
- selecting a similarity behavior group for the ego driver; and
- supplementing the normal driving behavior group and the tired driving behavior group based on the normal/tired driving clusters of drivers in the similarity behavior group.

9. The method of claim 6, further comprising determining the refueling pattern preference by:
- extracting, from the historical data, a distribution of fuel level amounts before refueling;
- determining a posterior distribution of the fuel level amounts before refueling based on Bayesian inference; and
- determining the refueling pattern preference as a summation of a mean value and a standard deviation value over the distribution and the posterior distribution.

10. The method of claim 6, wherein the rest stop characteristic preferences include one or more of:
- a detour distance traveled to the rest stop;
- a type of restaurant located at the rest stop; or
- a presence of a gas station at the rest stop.

11. A non-transitory computer-readable medium for determining and providing a rest stop recommendation, including instructions that, when executed by one or more processors, cause the one or more processors to:
- monitor, over a period of time, driving behavior of an ego driver driving a vehicle;
- store information indicating the driving behavior as historical data;
- determine, based at least in part on the historical data, a driver tiredness state, a continuous driving length preference, and a refueling pattern preference, wherein the instructions to determine the continuous driving length preference:
  - extract, from the historical data, a distribution of sequences of continuous drive time lengths before a rest;
  - determine a posterior distribution of the continuous drive time lengths before the rest based on Bayesian inference; and
  - determine the continuous driving length preference as a summation of a mean value and a standard deviation value over the distribution and the posterior distribution;
- determine a time to recommend a rest stop based at least in part on the driver tiredness state, the continuous driving length preference, and the refueling pattern preference;
- extract, from a map database, a plurality of rest stops within a predetermined radius of a position of the vehicle;
- determine rest stop characteristic preferences based at least in part on the historical data;

select one or more potential rest stops from among the plurality of rest stops based at least in part on the rest stop characteristic preferences;
present the one or more potential rest stops to the ego driver in a recommendation;
determine one or more routes, respectively, for the one or more potential rest stops based at least in part on the historical data;
receive, via an input system, a selection of a route of the one or more routes; and
communicate with at least one vehicle system to perform, in an automated manner, at least a portion of a navigation of the vehicle along the route,
wherein the at least one vehicle system comprises at least one of a propulsion system, a braking system, a steering system, a throttle system, a transmission system, a signaling system, or a navigation system.

12. The non-transitory computer-readable medium of claim 11, wherein the instructions to determine the driver tiredness state comprises instructions to:
define driving sequences in the historical data;
cluster at least a portion of the driving sequences into a normal driving behavior group and a tired driving behavior group;
process a current driving sequence for cluster classification; and
determine the driver tiredness state is 'normal' when the current driving sequence is classified in the normal driving behavior group, or 'tired' when the current driving sequence is classified in the tired driving behavior group.

13. The non-transitory computer-readable medium of claim 12, further comprising instructions to, prior to processing the current driving sequence for cluster classification:
obtain supplemental cluster data indicating normal/tired driving clusters for a plurality of drivers;
cluster the plurality of drivers into similarity behavior groups;
select a similarity behavior group for the ego driver; and
supplement the normal driving behavior group and the tired driving behavior group based on the normal/tired driving clusters of drivers in the similarity behavior group.

14. The non-transitory computer-readable medium of claim 11, further comprising instructions to determine the refueling pattern preference by:

extracting, from the historical data, a distribution of fuel level amounts before refueling;
determining a posterior distribution of the fuel level amounts before refueling based on Bayesian inference; and
determining the refueling pattern preference as a summation of a mean value and a standard deviation value over the distribution and the posterior distribution.

15. The rest stop recommendation system of claim 1, wherein at least one of the one or more routes includes at least one of the rest stop characteristic preferences, the at least one of the rest stop characteristic preferences being at a location other than the rest stop.

16. The method of claim 6, wherein at least one of the one or more routes includes at least one of the rest stop characteristic preferences, the at least one of the rest stop characteristic preferences being at a location other than the rest stop.

17. The non-transitory computer-readable medium of claim 11, wherein at least one of the one or more routes includes at least one of the rest stop characteristic preferences, the at least one of the rest stop characteristic preferences being at a location other than the rest stop.

18. A vehicle, comprising:
a propulsion system;
a processor; and
a memory storing a module including instructions that cause the processor to:
store historical data about a driving behavior of a driver of the vehicle;
extract, from the historical data, a distribution of sequences of continuous drive time lengths before a rest;
determine a posterior distribution of the continuous drive time lengths before the rest based on Bayesian inference;
determine the continuous driving length preference as a summation of a mean value and a standard deviation value over the distribution and the posterior distribution;
extract, from a map, a route to a rest stop location; and
perform, in an automated manner, using the propulsion system, and based on the continuous driving length preference, a portion of a navigation of the vehicle to the rest stop location.

* * * * *